(12) United States Patent
Ramachandran et al.

(10) Patent No.: US 12,167,945 B2
(45) Date of Patent: Dec. 17, 2024

(54) PATIENT ID AND SAMPLE ID WORKFLOW METHODS AND APPARATUS FOR FACILITATING DIAGNOSTIC TESTING

(71) Applicant: Siemens Healthcare Diagnostics Inc., Tarrytown, NY (US)

(72) Inventors: Prabhu Ramachandran, Newton, MA (US); Karen Lim, Pasadena, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 582 days.

(21) Appl. No.: 17/310,236

(22) PCT Filed: Feb. 3, 2020

(86) PCT No.: PCT/US2020/016352
§ 371 (c)(1),
(2) Date: Jul. 27, 2021

(87) PCT Pub. No.: WO2020/163214
PCT Pub. Date: Aug. 13, 2020

(65) Prior Publication Data
US 2022/0047355 A1 Feb. 17, 2022

Related U.S. Application Data

(60) Provisional application No. 62/801,942, filed on Feb. 6, 2019.

(51) Int. Cl.
*A61B 90/96* (2016.01)
*G16H 10/40* (2018.01)
(Continued)

(52) U.S. Cl.
CPC ............. *A61B 90/96* (2016.02); *G16H 10/40* (2018.01); *G16H 10/60* (2018.01); *G16H 40/67* (2018.01)

(58) Field of Classification Search
CPC ........ A61B 90/96; G16H 40/67; G16H 10/40; G16H 10/60
(Continued)

(56) References Cited

U.S. PATENT DOCUMENTS

D497,617 S 10/2004 Decombe et al.
D708,203 S 7/2014 Johnson
(Continued)

FOREIGN PATENT DOCUMENTS

CA 2901016 A1 8/2014
JP 2010110499 A 5/2010
(Continued)

OTHER PUBLICATIONS

European Search Report and Search Opinion of European Application No. 20752748.2 dated Feb. 21, 2022.
(Continued)

*Primary Examiner* — Michael Tomaszewski

(57) ABSTRACT

A point of care system includes an instrument data manager (IDM) configured to communicate with a diagnostic engine and to (1) obtain identification (ID) information of a patient for which a test is to be performed; (2) obtain ID information of a diagnostic consumable to be used to collect a sample from the patient; (3) link the obtained patient ID information with the obtained diagnostic consumable ID information; and (4) restrict testing using the diagnostic engine by (a) prior to performing a test on a sample collected with a diagnostic consumable, determine ID information of the diagnostic consumable at the diagnostic engine; (b) determine whether the diagnostic consumable is linked with patient information within the IDM; and (c) if so, allow the diagnostic engine to perform a test on the sample collected with the diagnostic consumable. Numerous other embodiments are provided.

20 Claims, 9 Drawing Sheets

(51) Int. Cl.
*G16H 10/60* (2018.01)
*G16H 40/67* (2018.01)

(58) Field of Classification Search
USPC .......................................................... 705/2–3
See application file for complete search history.

(56) References Cited

U.S. PATENT DOCUMENTS

| | | | |
|---|---|---|---|
| D717,822 S | | 11/2014 | Brotman et al. |
| D737,278 S | | 8/2015 | Shin et al. |
| D760,742 S | | 7/2016 | Rawlins et al. |
| D762,230 S | | 7/2016 | Kaplan et al. |
| D771,076 S | | 11/2016 | Butcher et al. |
| D776,717 S | | 1/2017 | Asai |
| D795,917 S | | 8/2017 | Escutia et al. |
| D800,163 S | | 10/2017 | Tsukahara |
| D807,376 S | | 1/2018 | Mizono et al. |
| D808,974 S | | 1/2018 | Chiappone et al. |
| D821,438 S | | 6/2018 | Denis et al. |
| D824,416 S | | 7/2018 | Memmelaar, Jr. et al. |
| D824,417 S | | 7/2018 | Narinedhat |
| D826,971 S | | 8/2018 | Fleischmann et al. |
| D839,293 S | | 1/2019 | Tsuji et al. |
| D839,888 S | | 2/2019 | Yun |
| D843,392 S | | 3/2019 | Timmer et al. |
| D845,969 S | | 4/2019 | Malahy et al. |
| D848,466 S | | 5/2019 | Mizono et al. |
| D849,039 S | | 5/2019 | Huh et al. |
| D854,035 S | | 7/2019 | Escutia et al. |
| D872,102 S | | 1/2020 | Wang et al. |
| D875,751 S | | 2/2020 | Kim et al. |
| D902,946 S | | 11/2020 | Doti et al. |
| D905,074 S | | 12/2020 | Lin et al. |
| D934,899 S | | 11/2021 | Bennett et al. |
| D942,641 S | * | 2/2022 | Reavis, Jr. .................. D24/216 |
| D964,379 S | | 9/2022 | Mitsumori |
| D964,381 S | | 9/2022 | Li et al. |
| D967,850 S | | 10/2022 | Narasaki et al. |
| 2003/0092186 A1 | * | 5/2003 | Pressman ............ B01L 3/50825 436/178 |
| 2005/0060188 A1 | * | 3/2005 | Valley ................ G16H 40/20 705/2 |
| 2007/0053793 A1 | * | 3/2007 | Maeda .................. G06F 17/00 422/63 |
| 2007/0233035 A1 | * | 10/2007 | Wehba ................ G16H 40/40 604/500 |
| 2009/0227897 A1 | * | 9/2009 | Wendt ................ A61B 5/15186 600/583 |
| 2010/0053620 A1 | * | 3/2010 | Ogawa ................ G01N 21/255 356/436 |
| 2011/0035237 A1 | * | 2/2011 | Ariyoshi ................ G16H 10/40 705/3 |
| 2012/0109529 A1 | * | 5/2012 | Ariyoshi ................ G01N 35/026 702/19 |
| 2012/0233679 A1 | | 9/2012 | Shedrinsky |
| 2013/0080071 A1 | * | 3/2013 | Holmes .................. G16B 50/00 702/19 |
| 2013/0117042 A1 | * | 5/2013 | Tajima ............... G01N 35/0092 705/2 |
| 2013/0166315 A1 | * | 6/2013 | Fonseca ................ G16H 10/40 705/2 |
| 2013/0197943 A1 | * | 8/2013 | Conlin ................ G06F 16/2471 705/2 |
| 2013/0260414 A1 | | 10/2013 | Yao et al. |
| 2014/0081657 A1 | * | 3/2014 | Neuvonen ............... G16Z 99/00 705/3 |
| 2014/0337056 A1 | * | 11/2014 | Rampetsreiter ....... G06F 16/284 235/375 |
| 2015/0209114 A1 | * | 7/2015 | Burkholz ................ A61M 5/14 600/584 |
| 2015/0209510 A1 | * | 7/2015 | Burkholz ................ G06F 3/011 604/93.01 |
| 2016/0019349 A1 | * | 1/2016 | Ross ....................... G16Z 99/00 705/3 |
| 2016/0080548 A1 | | 3/2016 | Erickson et al. |
| 2016/0321421 A1 | * | 11/2016 | Delgrande ............. H04L 67/12 |
| 2016/0321581 A1 | * | 11/2016 | Delgrande ......... G06Q 10/0633 |
| 2017/0021349 A1 | * | 1/2017 | Tieman .................. B01L 3/545 |
| 2017/0220775 A1 | * | 8/2017 | De La Torre-Bueno .................... G16H 30/20 |
| 2019/0117888 A1 | * | 4/2019 | Burkholz ............. G02B 27/017 |
| 2020/0286621 A1 | * | 9/2020 | Lim ...................... G16H 40/20 |
| 2020/0388389 A1 | * | 12/2020 | Deshpande ........... G16H 10/40 |
| 2021/0295959 A1 | * | 9/2021 | Delgrande ............ G16H 40/63 |

FOREIGN PATENT DOCUMENTS

| | | | | |
|---|---|---|---|---|
| JP | 2013017820 A | | 1/2013 | |
| JP | 2014062917 A | | 4/2014 | |
| WO | WO-2013052990 A1 | * | 4/2013 | .......... G06F 16/284 |

OTHER PUBLICATIONS

International Search Report and Written Opinion of International Application No. PCT/US2020/016352 dated Apr. 14, 2020.

* cited by examiner

200

| PATIENT ID | NAME | DATE OF BIRTH | ADDRESS |
|---|---|---|---|
| PID123456780 | SMITH, JOE | 01/01/1935 | White Plains, NY |
| PID223456780 | SMITH, JANE | 02/02/1940 | Hawthorne, NY |
| PID323456780 | DOE, JOHN | 03/03/1945 | Tarrytown, NY |
| PID423456780 | DOE, JANE | 04/04/1950 | Croton, NY |
| PID523456780 | SMITH, JACK | 05/05/1955 | Scarsdale, NY |
| PID623456780 | SMITH, SALLY | 06/06/1960 | Ridgefield, CT |

| SAMPLE CONSUMABLE ID | TEST TO PERFORM |
|---|---|
| SID1234567890 | BLOOD GAS DIAGNOSTIC |
| SID2234567890 | CARDIAC DIAGNOSTIC |
| SID3234567890 | COAGULATION DIAGNOSTIC |
| SID4234567890 | DIABETES DIAGNOSTIC |
| SID5234567890 | URINALYSIS DIAGNOSTIC |
| SID5234567890 | CARDIAC DIAGNOSTIC |

FIG. 2B

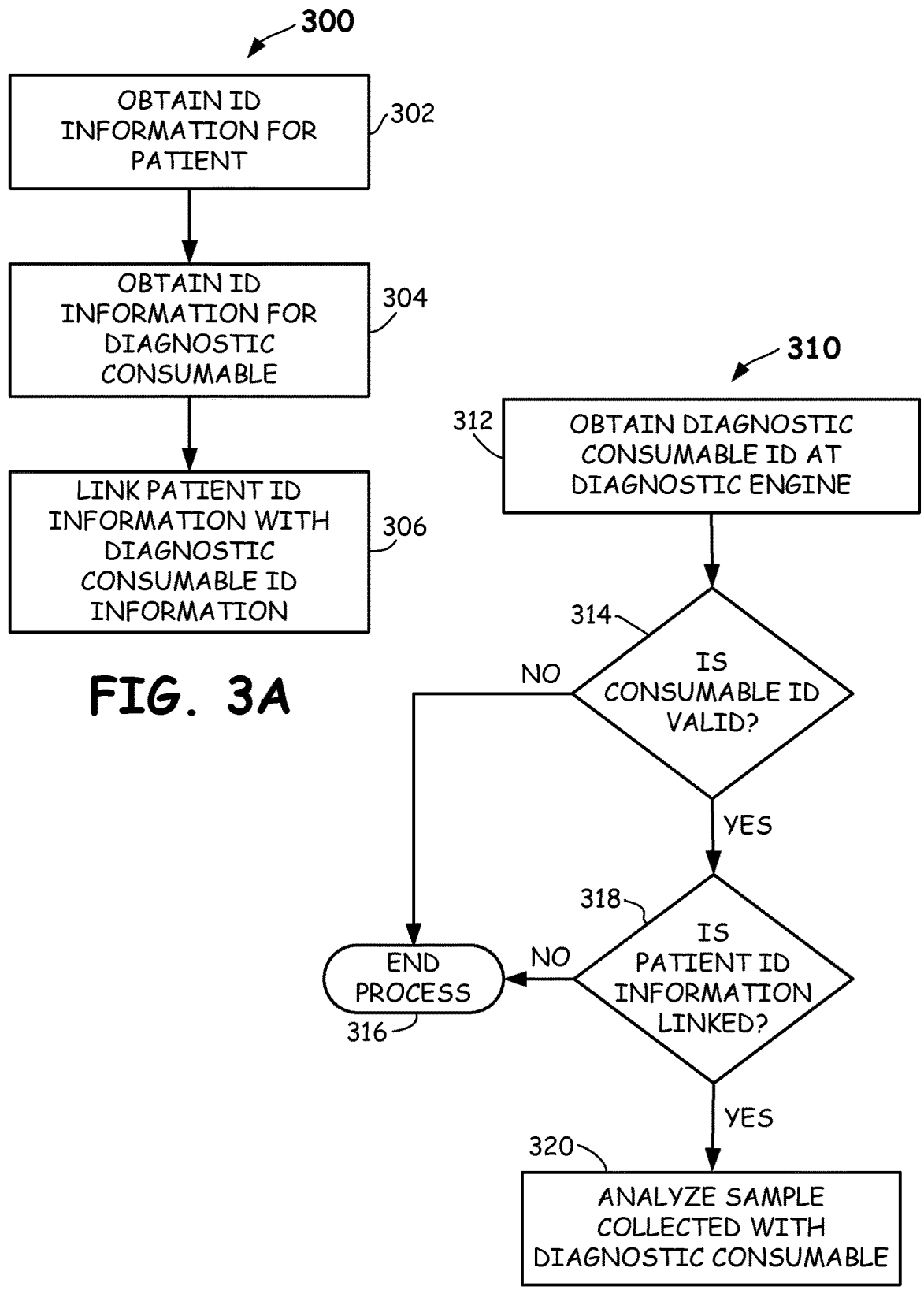

400a

```
04:21 PM 01/19/2018
→] Login
≡ Home

Clinical
       Start
         ⓘ

Ready
```

```
04:21 PM 01/19/2018
→] Login
◁ Login

Operator ID:
OID1234567890
Password
********************

Scan
Login
```

```
04:21 PM 01/19/2018
↩ OID1234567890
◁ Patient
Patient ID
PID1234567890
Name                    >
Smith
DOB
07/04/1970
Gender
Male Scan    Patient List
Home    |    Continue
```

```
04:21 PM 01/19/2018
↩ OID1234567890
◁ Sample
Sample ID
SID1234567890

Scan
Home    |    Continue
```

FIG. 4D

PATIENT ID AND SAMPLE ID WORKFLOW METHODS AND APPARATUS FOR FACILITATING DIAGNOSTIC TESTING

The subject application claims benefit under 35 USC § 119(e) of U.S. provisional Application No. 62/801,942, filed Feb. 6, 2019. The entire contents of the above-referenced patent application are hereby expressly incorporated herein by reference.

FIELD

The present application relates to diagnostic testing, and more particularly to patient identification (ID) and sample ID workflow methods and apparatus for facilitating diagnostic testing.

BACKGROUND

Point of care testing may be defined as medical diagnostic testing that is performed at a location where care or other treatment is provided. Point of care testing may also be referred to as near-patient testing, remote testing, satellite testing, and rapid diagnostics testing. Point of care test results may be made available relatively quickly so that they can be acted upon without delay. This increases the likelihood that the patient, physician, and care team will receive test results quicker, which allows for better and more immediate clinical management decisions to be made.

Improved systems, methods and apparatus for point of care testing are desired.

SUMMARY

In some embodiments, a point of care system is provided that includes an instrument data manager (IDM) configured to communicate with a diagnostic engine, the IDM being configured to (1) obtain identification (ID) information of a patient for which a test is to be performed using the diagnostic engine; (2) obtain ID information of a diagnostic consumable to be used to collect a sample from the patient; (3) link the obtained patient ID information with the obtained diagnostic consumable ID information; and (4) restrict testing using the diagnostic engine by (a) prior to performing a test on a sample collected with a diagnostic consumable, determine ID information of the diagnostic consumable at the diagnostic engine; (b) determine whether the diagnostic consumable is linked with patient ID information within the IDM; and (c) if the diagnostic consumable is linked with patient ID information within the IDM, allow the diagnostic engine to perform a test on the sample collected with the diagnostic consumable.

In some embodiments, a method of providing point of care diagnostic testing using a diagnostic engine includes employing an instrument data manager (IDM) to (1) obtain identification (ID) information of a patient for which a test is to be performed using the diagnostic engine; (2) obtain ID information of a diagnostic consumable to be used to collect a sample from the patient; and (3) link the obtained patient ID information with the obtained diagnostic consumable ID information. The method further includes restricting testing using the diagnostic engine by (4) prior to performing a test on a sample collected with a diagnostic consumable, determining ID information of the diagnostic consumable at the diagnostic engine; (5) determining whether the diagnostic consumable is linked with patient ID information within the IDM; and (6) if the diagnostic consumable is linked with patient ID information within the IDM, allowing the diagnostic engine to perform a test on the sample collected with the diagnostic consumable.

In some embodiments, a method of providing point of care diagnostic testing using a diagnostic engine includes (1) obtaining identification (ID) information of a patient for which a test is to be performed using the diagnostic engine; (2) obtaining ID information of a diagnostic consumable to be used to collect a sample from the patient; (3) linking the patient ID information with the diagnostic consumable ID information; and (4) prior to performing a test on a sample collected with the diagnostic consumable (a) scanning ID information of the diagnostic consumable at the diagnostic engine; (b) determining whether the diagnostic consumable is linked with the patient ID information; and (c) if the diagnostic consumable is linked with the patient ID information, allowing the diagnostic engine to perform a test on the sample collected with the diagnostic consumable.

In some embodiments, a method of providing point of care diagnostic testing using a diagnostic engine includes (1) employing an instrument data manager (IDM) to obtain identification (ID) information of a patient for which a test is to be performed using the diagnostic engine; (2) employing the IDM to scan ID information of a diagnostic consumable to be used to collect a sample from the patient; (3) linking the patient ID information with the diagnostic consumable ID information within the IDM; and (4) prior to performing a test on a sample collected with a diagnostic consumable (a) scanning ID information of the diagnostic consumable at the diagnostic engine; (b) communicating the scanned ID information to the IDM; (c) confirming that the diagnostic consumable is linked with the patient ID information within the IDM; and (d) if the diagnostic consumable is linked with the patient ID information within the IDM, directing the diagnostic engine to perform a test on the sample collected with the diagnostic consumable.

In some embodiments, an instrument data manager (IDM) configured to control operation of a plurality of diagnostic engines includes (1) a display; (2) a processor coupled to the display; and (3) a memory coupled to the processor, the memory having stored therein a plurality of computer executable instructions that, when executed by the processor, cause the IDM to (a) provide a user interface through which the IDM obtains identification (ID) information for patients and ID information for diagnostic consumables; (b) after obtaining patient ID information and diagnostic consumable ID information with the user interface, link the diagnostic consumable ID information with the patient ID information; (c) receive diagnostic consumable ID information from the plurality of diagnostic engines; and (d) prevent testing of samples collected with diagnostic consumables at one or more of the plurality of diagnostic engines if diagnostic consumable ID information received from the one or more of the plurality of diagnostic engines is not linked to patient ID information within the IDM.

In some embodiments, a method is provided that is performed by an instrument data manager (IDM) in communication with a plurality of diagnostic engines, the IDM being configured to communicate with each of the plurality of diagnostic engines to enable a plurality of tests to be performed on a plurality of samples using the plurality of diagnostic engines. The method includes (1) obtaining, via a user interface of the IDM, identification (ID) information of a patient for which a test is to be performed; (2) obtaining, via the user interface of the IDM, ID information of a diagnostic consumable to be used to collect a sample from the patient; (3) linking, within the IDM, the obtained patient ID information with the obtained diagnostic consumable ID information; and (4) restricting testing using the plurality of diagnostic engines by (a) prior to allowing performance of a test on a sample collected with a diagnostic consumable within any of the plurality of diagnostic engines, receiving ID information of the diagnostic consumable from a diagnostic engine; (b) determining whether the diagnostic consumable ID information is linked with patient ID information within the IDM; and (c) if the diagnostic consumable ID information is linked with patient ID information within the IDM, allowing the diagnostic engine to perform the test on the sample collected with the diagnostic consumable.

In some embodiments, a point of care system is provided that includes (1) a diagnostic engine configured to perform a test on a sample and to generate a measured result based on the test on the sample; and (2) an instrument data manager (IDM) in electronic communication with the diagnostic engine, the IDM being configured to (a) obtain identification (ID) information of a patient for which a test is to be performed using the diagnostic engine; (b) obtain ID information of a diagnostic consumable to be used to collect a sample from the patient; (c) link the obtained patient ID information with the obtained diagnostic consumable ID information; and (d) restrict testing using the diagnostic engine by (i) prior to performing a test on a sample collected with a diagnostic consumable, determine ID information of the diagnostic consumable at the diagnostic engine; (ii) determine whether the diagnostic consumable is linked with patient ID information within the IDM; and (iii) if the diagnostic consumable is linked with patient ID information within the IDM, allow the diagnostic engine to perform a test on the sample collected with the diagnostic consumable.

Other features and aspects of the present invention will become more fully apparent from the following detailed description, the appended claims, and the accompanying drawings.

BRIEF DESCRIPTION OF THE DRAWINGS

FIG. 2A illustrates an example data structure of patient information in accordance with embodiments of the disclosure.

FIG. 2B illustrates an example data structure of diagnostic consumable information in accordance with embodiments of the disclosure.

FIG. 3A illustrates an example method for collecting patient ID information and diagnostic consumable ID information, and linking patient ID information and diagnostic consumable ID information in accordance with embodiments disclosed herein.

FIG. 3B illustrates an example method for ensuring patient ID information and diagnostic consumable ID information are linked before allowing testing with a diagnostic engine in accordance with embodiments disclosed herein.

DETAILED DESCRIPTION

Figure 1A:
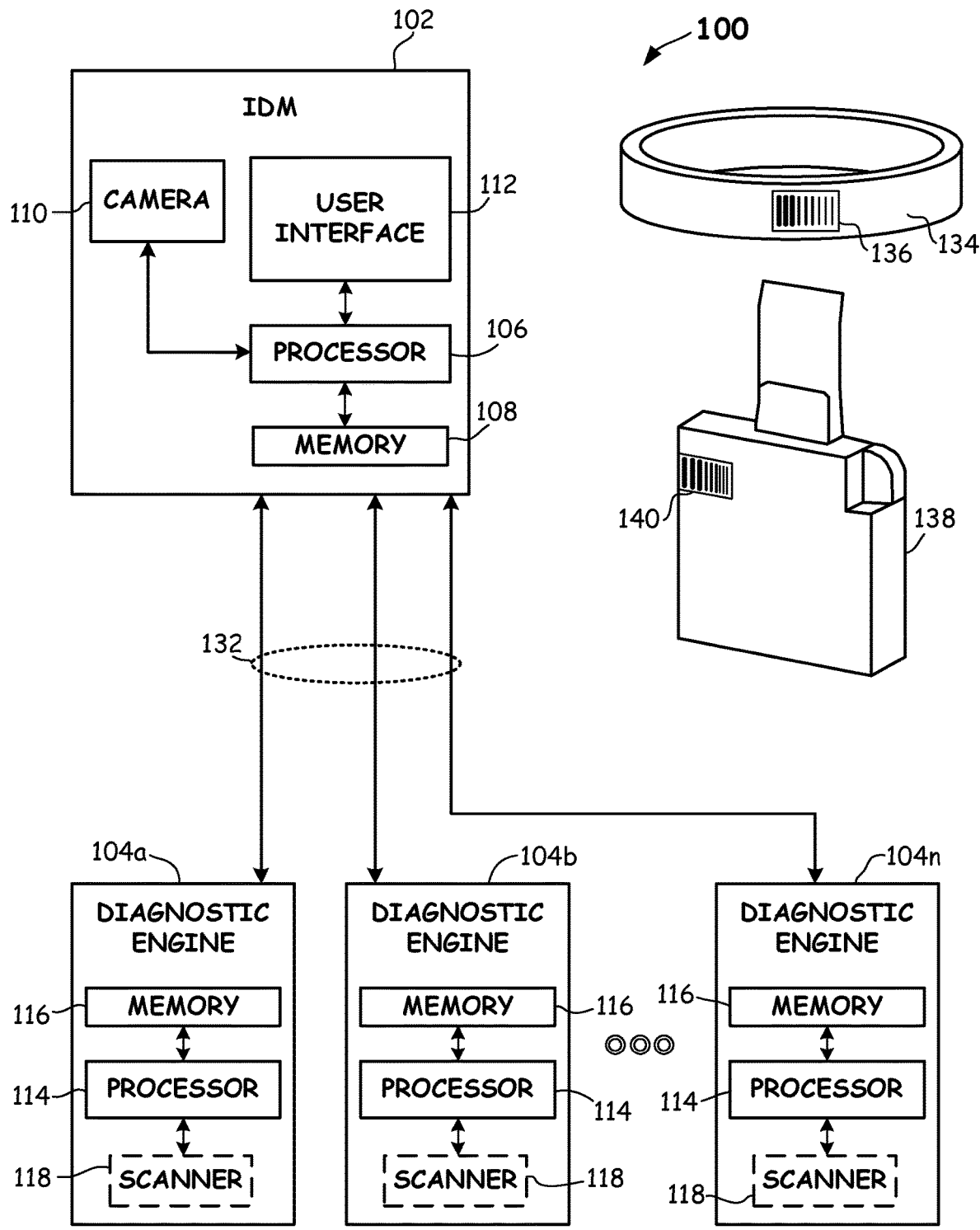
FIG. 1A illustrates an example point of care system provided in accordance with embodiments of the disclosure.

As stated above, point of care systems allow patients, physicians, and care teams to receive test results quickly, which allows for better and more immediate clinical management decisions to be made. However, to be beneficial, test results must be accurately associated with the correct patient. This becomes more difficult in a busy clinical setting in which numerous tests are performed on many patients. Embodiments provided herein help ensure that test results performed during point of care testing are associated with the correct patient(s).

Point of care testing may be defined as medical diagnostic testing that is performed at a location where care or other treatment is provided. A point of care system or device may be located, for example, in a hospital, nursing home, clinic, or in the home of an individual patient. Point of care testing may also be referred to herein as near-patient testing, remote testing, satellite testing, and/or rapid diagnostics testing.

During point of care testing, a patient sample is collected and analyzed using a testing device referred to herein as a diagnostic engine. Example patient samples may include urine, blood, plasma, saliva, cerebrospinal fluid, pleural fluid, nasopharyngeal, or the like. Patient samples are collected using a diagnostic consumable which may include, for example, a sample cartridge or other sample container in which blood or another bodily fluid is stored, a urine cup, a test strip such as a urine or lateral flow strip, etc. Such diagnostic consumables are typically, but need not be, one-time-use consumables.

In accordance with embodiments provided herein, diagnostic engines used for testing may be controlled by a central interface unit, referred to as an instrument data manager (IDM). For example, U.S. Provisional Patent Application No. 62/588,689, filed Nov. 20, 2017, titled "Multiple Diagnostic Engine Environment," and which is hereby incorporated by reference herein in its entirety for all purposes, describes a point of care system which includes a plurality of diagnostic engines and an IDM in electronic communication with each of the plurality of diagnostic engines. Each of the plurality of diagnostic engines may perform testing on a sample collected with a diagnostic consumable received from a patient. The IDM may be configured to communicate with each of the plurality of diagnostic engines to enable a plurality of tests to be performed on multiple different samples substantially simultaneously by a plurality of users using the plurality of diagnostic engines and to present a single user interface for managing testing by the plurality of diagnostic engines and for receiving measured results of tests performed by each of the plurality of diagnostic engines.

In some example embodiments described herein, a point of care system may include one or more diagnostic engines controlled and/or interfaced with an IDM. The IDM may be employed to obtain identification (ID) information of a patient for which a test is to be performed. The IDM also may be used to obtain ID information of a diagnostic consumable to be used to collect and/or store a sample from the patient. In some embodiments, the IDM may use a camera to image a barcode on a patient wrist band to obtain patient ID information and/or to image a barcode on the diagnostic consumable to obtain diagnostic consumable ID information. The IDM then links the patient ID information with the diagnostic consumable ID information. For example, the patient ID information and diagnostic consumable ID information may be linked together in a memory and/or database (or other data structure) within the IDM. Each patient to be tested using diagnostic engines may have one or more diagnostic consumables linked with the patient. For example, patient ID information and diagnostic consumable ID information may be linked just prior to sample collection.

After sample collection with the diagnostic consumable and prior to performing a test on a patient's sample using a diagnostic engine within the point of care system, ID information of the diagnostic consumable with the sample to be tested is scanned at the diagnostic engine. For example, a barcode scanner within or near the diagnostic engine may be used to obtain the diagnostic consumable ID information. Alternatively, a camera or other scanner within the diagnostic engine may scan the diagnostic consumable as the diagnostic consumable is loaded into the diagnostic engine. This diagnostic consumable ID information is provided to the IDM, which determines whether the diagnostic consumable is linked with a patient (e.g., whether the scanned diagnostic consumable ID information is linked with patient ID information within the IDM). If the diagnostic consumable ID information is linked with patient ID information within the IDM, the IDM allows the diagnostic engine to perform a test on the sample collected with the diagnostic consumable. If the diagnostic consumable ID information is not linked with patient ID information within the IDM, the IDM prevents the diagnostic engine from performing a test on the sample collected with the diagnostic consumable.

In some embodiments, a diagnostic consumable may be a cartridge or container which holds a sample and which is placed directly into a diagnostic engine. Alternatively, a diagnostic consumable may merely hold a sample prior to the sample being analyzed by a diagnostic engine. For example, a urine cup may include a diagnostic consumable ID that is linked with patient ID information as described herein. At a diagnostic engine, the diagnostic consumable ID of the urine cup may be scanned to ensure that the urine cup is linked with patient information within the IDM prior to testing. A test strip may then be used to collect a portion of the sample from the urine cup for testing within the diagnostic engine. In some embodiments, the test strip need not include a barcode or other ID information that is linked with patient information within the IDM. However, in other embodiments, test strips may include diagnostic consumable ID information (e.g., a scannable barcode) that must be linked with patient ID information before being analyzed with a diagnostic engine.

A diagnostic consumable may include a vessel that retains a patient sample. In some embodiments, a diagnostic consumable containing a sample may itself be inserted into a diagnostic engine for testing. In one or more other embodiments, a diagnostic consumable may hold a sample prior to the use of another diagnostic consumable. For example, a first diagnostic consumable may be a urine cup which holds a sample prior to application of a second diagnostic consumable such as a urine strip. The urine strip may then be analyzed by a diagnostic engine. In such embodiments in which two or more diagnostic consumables are used to house and/or provide a sample to a diagnostic engine, each diagnostic consumable may include ID information (e.g., a scannable bar code) or a subset of the diagnostic consumables may include ID information that may be linked with patient ID information and that may be scanned prior to testing at a diagnostic engine. In some embodiments, a diagnostic consumable may hold and provide a sample directly to a diagnostic engine. For example, a blood gas analyzer may employ a needle to draw blood out of a diagnostic consumable (e.g., a syringe).

By linking patient ID information and diagnostic consumable ID information at the time the sample is taken, and then confirming that any diagnostic consumable having a sample to be tested is linked with a patient within the IDM prior to testing with a diagnostic engine, test results are known to be associated with the correct patient(s). These and other embodiments are described below with reference to FIGS. 1-4P.

FIG. 1A illustrates an example point of care (POC) system 100 provided in accordance with embodiments of the disclosure. With reference to FIG. 1A, POC system 100 may include an IDM 102 in communication with one or more diagnostic engines 104a-n. Any number of diagnostic engines may be employed (e.g., 1, 2, 3, 5, 10, etc.).

In some embodiments, IDM 102 may include a processer 106 coupled to a memory 108, a camera 110 and a user interface 112. Processor 106 may be a computational resource such as, but not limited to, a microprocessor, a microcontroller, an embedded microcontroller, a digital signal processor (DSP), a field programmable gate array (FPGA) configured to perform as a microcontroller, or the like.

Memory 108 may be any suitable type of memory, such as, but not limited to, one or more of a volatile memory and/or a non-volatile memory. For example, memory 108 may include a combination of different types of memory such as volatile memory and non-volatile memory. Volatile memory may include, but is not limited to, a static random access memory (SRAM), or a dynamic random access memory (DRAM). Non-volatile memory may include, but is not limited to, an electrically programmable read-only memory (EPROM), an electrically erasable programmable read-only memory (EEPROM), a flash memory, etc. Memory 108 may have a plurality of instructions stored therein that, when executed by processor 106, cause processor 106 to perform various actions specified by one or more of the stored plurality of instructions.

Camera 110 may include any suitable imaging device capable of imaging a barcode or other identifying information of a patient name tag (e.g., a wrist band), a diagnostic consumable, etc., as described further below. In some embodiments, camera 110 may be a barcode reader in communication with IDM 102. For example, camera 110 may be a wireless (e.g., Bluetooth®, WIFI, or other wireless protocol) barcode reader.

User interface 112 may include one or more of a display screen, a touch panel and/or screen, an audio speaker, and a microphone, for example. User interface 112 may be controlled by the IDM 102, and functionality of user interface 112 may be implemented, at least in part, by computer-executable instructions (e.g., program code or software) stored in memory 108 and/or executed by processor 106 of IDM 102. In some embodiments, IDM 102 may receive one or more measured results from one or more diagnostic engines 102a-n, process the measured results to generate calculated results, and present the calculated results and/or other information, such as patient information, via user interface 112. For example, user interface 112 may be configured to present one or more calculated results to a user of user interface 112.

In some embodiments, user interface 112 may be diagnostic engine agnostic, meaning that it may be able to present results associated with any number of diagnostic engines and any type of diagnostic engine. User interface 112 may allow multiple diagnostic engines to be operated at the same time and using the same interface. In one or more embodiments, a user of user interface 112 may be able to begin a test, enter or view patient information, enter login credentials, view the time remaining on a particular test, and/or view the calculated results based on a test performed by a given diagnostic engine 102a-n.

User interface 112 may allow for common screens and elements between different types of diagnostic engines, improving efficiency of POC system 100 as a user of user interface 112 may only need to learn a single interface. Common elements may be presented on user interface 112. Additionally or alternatively, specific instructions such as product specific instructions may be presented on user interface 112 which may be accessed from the single home screen.

In some embodiments, user interface 112 may display the status or calculated results of a test. User interface 112 may display the status or calculated results of multiple tests simultaneously. For example, if a user is running a urine test on a first patient and a blood test on a second patient, the user may be able to view one or more of the status or the calculated results of the urine test and the blood test on a single screen. This may be the case even when the urine test is being performed on a urinalysis diagnostic engine manufactured by a first company and the blood test is being performed on a blood testing diagnostic engine manufactured by a second company. In one example, user interface 112 may be configured to simultaneously display calculated results associated with two different users of user interface 112. For example, user interface 112 may simultaneously display a blood test result for a first patient that was initiated by a first user of user interface 112 and a urine test result for the first patient or for a second patient that was initiated by a second user of user interface 112.

In some embodiments, IDM 102 may include one or more other components such as removable storage, a local printer, or the like (not shown).

Diagnostic engines 104a-n may perform one or more tests. For example, diagnostic engines 104a-n may perform one or more tests to determine one or more characteristics of a sample, such as a bodily fluid sample. In some embodiments, one or more diagnostic engines 104a-n may be a diabetes diagnostic engine configured to determine one or more characteristics of a blood sample, such as an HbA1c level associated with the blood sample, or may be a urinalysis diagnostic engine configured to determine one or more characteristics of a urine sample, such as the presence of one or more metabolites in that urine sample. Other diagnostic engines may be used.

Each diagnostic engine 104a-n may include a processor 114 coupled to a memory 116. Optionally a scanner 118 (e.g., a camera, a barcode reader, etc.) also may be coupled to the processor 114. Other example components, that may be included in one or more of diagnostic engines 104a-n are illustrated in diagnostic engine 104 of FIG. 1B (e.g., wireless circuitry 120, heating element 122, mixing means 124, optical sensor 126, pump 128, reagents 130 and/or the like). It is understood that a given one of diagnostic engines 104a-n may optionally comprise any number or any combination of these elements. For example, a diagnostic engine may comprise multiple optical sensors 126 but may not comprise pump 128. It is further understood that a diagnostic engine 104a-n may comprise other components not shown in the figures or described herein, such as a separation means or any other components as would be understood by a person skilled in the art. In addition, a first type of diagnostic engine (e.g., a diabetes diagnostic engine) may comprise a different number and/or a different combination of components than a second type of diagnostic engine (e.g., a urinalysis diagnostic engine).

Processor 114 may be a computational resource such as, but not limited to, a microprocessor, a microcontroller, an embedded microcontroller, a DSP, a FPGA configured to perform as a microcontroller, or the like. Memory 116 may be any suitable type of memory, such as but not limited to, one or more of a volatile memory and/or a non-volatile memory. For example, memory 116 may include a combination of different types of memory such as volatile memory and non-volatile memory. Memory 116 may have a plurality of instructions stored therein that, when executed by processor 114, cause processor 114 to perform various actions specified by one or more of the stored plurality of instructions.

Processor 114 may be configured to process a sample. For example, processor 114 may be configured to receive an instruction from a user to perform a test on a sample (e.g., contained on or in a diagnostic consumable) inserted into a diagnostic engine 104a-n and to output one or more values representing a measured result of the test on that sample. In one embodiment, processor 114 may be a real-time processor configured to generate one or more measurements within a given time period, such as ten seconds. Processor 114 may additionally or alternatively be a non-real time processor configured to generate measured results based on the measurements from the test samples. In one example, one or more of diagnostic engines 104a-n may comprise multiple processors, such as a real-time processor configured to obtain measurements in real-time and a non-real time processor configured to process the measurements to generate measured results.

Processor 114 may control the various components of a diagnostic engine 104a-n (e.g., heating elements 122, mixing means 124, optical sensors 126, pumps 128, reagents 130, etc.,) and may receive feedback from those components. Processor 114 may adjust one or more characteristics of a diagnostic engine 104a-n accordingly (in real-time) to keep the diagnostic engine 104a-n within the proper operating conditions and may obtain the measured results of a test performed by the diagnostic engine 104a-n.

Referring again to FIG. 1A, memory 116 of IDM 102 may be configured to store information received or generated by one or more of diagnostic engines 104a-n. For example, memory 116 may be configured to store one or more values representing a measured result of a test performed by a diagnostic engines 104a-n. In one embodiment, one or more diagnostic engines 104a-n may comprise limited processing and memory capabilities such that the diagnostic engine 104a-n is configured only to process a particular type of sample, store one or more values representing a measurement and/or measured result of the test on that sample in memory 116, and to send the measured results to IDM 102.

Wireless circuitry 120 (FIG. 1B) may enable a diagnostic engine 104a-n to communicate with one or more other components of POC system 100. For example, wireless circuitry 120 may enable a diagnostic engine 104a-n to communicate measured results over a Bluetooth® or WiFi connection to IDM 102 (which may also include wireless circuitry, not separately shown). The information may additionally or alternatively be communicated to a printer, an informatics management program, or any other type of information system (not separately shown).

Figure 1B:
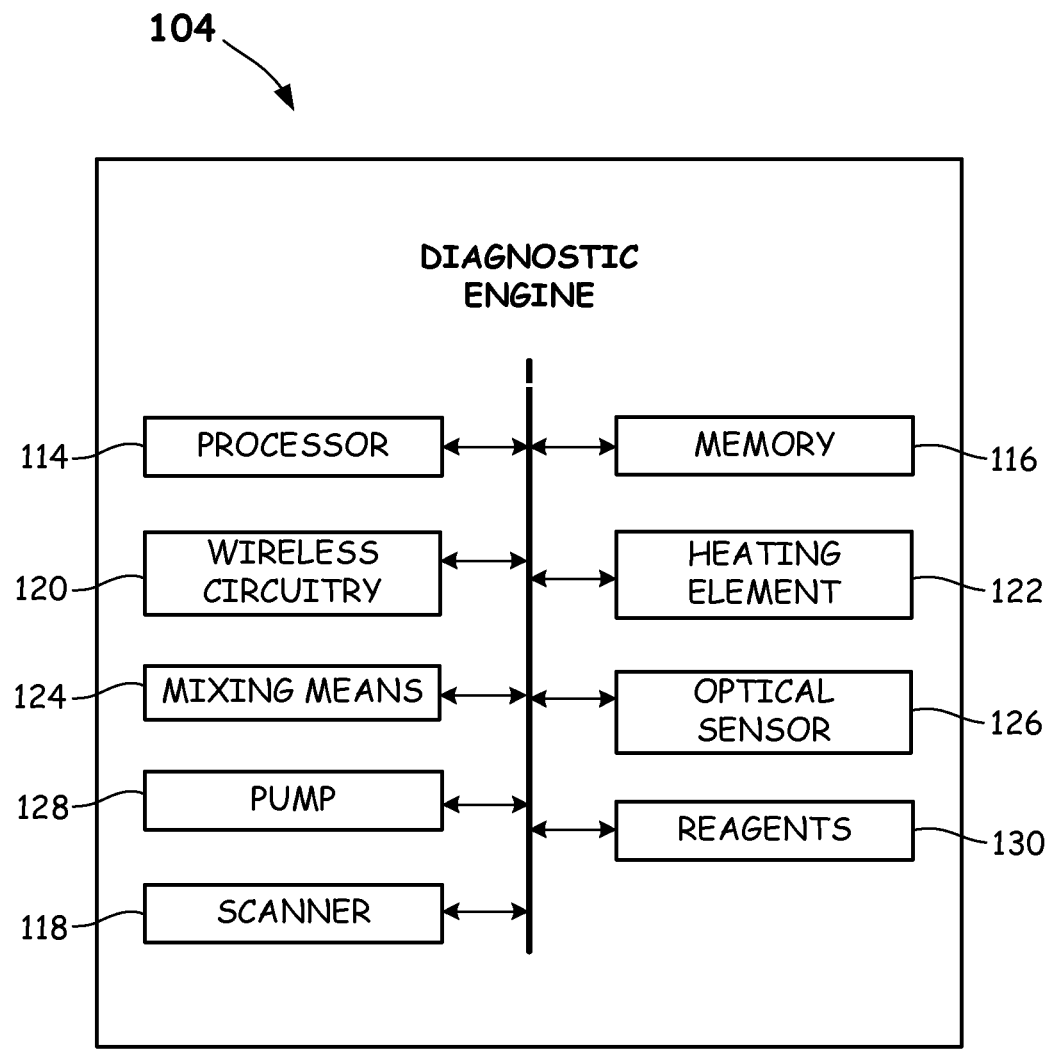
FIG. 1B illustrates an example diagnostic engine provided in accordance with embodiments of the disclosure.

As described, one or more of diagnostic engines 104a-n may comprise one or more components which may be in communication with processor 114 and which may be controlled by processor 114. For example, and as illustrated in FIG. 1B, a diagnostic engine 104a-n may comprise one or more of heating element 122 configured to heat a test sample, mixing means 124 configured to mix one or more components of the test sample, optical sensor 126 configured to determine one or more optical characteristics of the test sample, and pump 128 configured to move at least a portion of the sample from one location to another in the diagnostic engine 104a-n.

In some embodiments, diagnostic engines 104a-n may contain not only the physical components (e.g., heating element 122, mixing means 124, optical sensor 126, pump 128, reagent 130 and/or the like), but may also control the series of steps in which use of those components are utilized to obtain a measured result. For example, a diabetes diagnostic engine may mix a sample using mixing means 124, heat the sample to a desired temperature (e.g., 80 degrees Celsius) using the heating element 122, mix the sample a second time using mixing means 124, and take an optical reading of the sample using optical sensor 126.

Each diagnostic engines 104a-n may be configured to receive a sample in the form of a diagnostic consumable (e.g., a sample cartridge in which blood or another bodily fluid is stored, a test strip such as a urine or lateral flow strip, etc.). A diagnostic engine may be configured to come into direct contact with the sample during the test. Examples of these types of diagnostic engines include so called "bench top" blood gas analyzers (such as the RapidPoint 500, sold by Siemens Healthcare Diagnostics Inc., of Tarrytown, N.Y.) and automated urine chemistry analyzers (such as the Clinitek Novus, sold by Siemens Healthcare Diagnostics Inc. of Tarrytown, N.Y.). Alternatively, a diagnostic engine 104a-n, and physical components thereof, may not come into contact with the sample directly, but rather indirectly (e.g., optically).

A sample may be obtained from a patient using any one or a combination of methods known in the art. For example, in order to obtain a blood sample, a syringe can be used to withdraw blood from a vein of the patient. Additionally or alternatively, the blood sample can be separated (e.g., by centrifugation) to isolate and obtain a serum sample. A blood sample can additionally or optionally be obtained by lightly pricking one of the subject's fingers (e.g., with a sterile needle) and then collecting a desired volume of blood.

Following collection of a sample, the sample may be placed in a sample container or other consumable, collectively referred to herein as a diagnostic consumable, configured to be received by a given one of diagnostic engines 104a-n. For example, a diagnostic consumable may be a plastic or glass container configured to receive a certain volume of the sample, or may be a test strip configured to receive a minor amount of the sample. It is understood that a diagnostic consumable may comprise any type of container configured to receive any volume of a sample capable of being inserted into a diagnostic engine 104a-n.

Bodily fluids capable of being tested by one or more of diagnostic engines 104a-n include but are not limited to urine, blood, plasma, saliva, cerebrospinal fluid, pleural fluid, nasopharyngeal, and the like. Blood samples may be routinely analyzed to obtain measurements of the partial pressures of $CO_2$ and $O_2$ and/or concentrations of electrolytes and/or metabolites in the blood. A number of different diagnostic engines may be provided for making such measurements utilizing rigid layered sensor assemblies and electrical circuits. Such sensor assemblies may be used to assess the condition of medical patients through primary clinical indications, for example, through monitoring of $pCO_2$, $pO_2$, pH, Na+, K+, $Ca_2$+, Cl−, glucose, lactate, and hemoglobin values. However, it is understood that the samples are not limited to these types of samples and that diagnostic engines 104a-n may be configured to process any types of samples.

A diagnostic engine 104a-n may include a chemical sensor. For example, a diagnostic engine 104a-n may comprise a chemical surface, an integrated circuit structure, a micro-electromechanical structure, an optical sensor, or another device responsive to chemical characteristics, such as a chemical type, blood gas level, pH level, existence of a particular chemical, amount of a particular chemical, or other characteristics. For example, a diagnostic engine 104a-n may comprise a chemical or biological recognition element with or without a permeable membrane and a signal transducer element, such as electrochemical (amperometry or potentiometry), electrical (ion-sensitive field effect transistor, conductance, impedance, potential, or current), optical (luminescence, fluorescence or refractive index), thermal and/or piezoelectric elements. An amplification or processing element may be integrated with an analyte responsive recognition element and/or the signal transducer element. Using membrane entrapment, physical adsorption, matrix entrapment, reaction chamber, covalent bonding, or another physical structure for exposure, a biological recognition phase (enzyme, antibody, receptor, DNA or other chemical) may interact with the analyte of interest to produce a charge or optical change at the sensor-transducer interface or electrode. Any now known or later developed chemical sensors, such as immunosensors, optrodes, chemical canaries, resonant mirrors, glucometers, biochips, and/or biocomputers, may be used.

POC system 100 may comprise multiple diagnostic engines 104a-n and/or multiple different types of diagnostic engines 104a-n. For example, POC system 100 may comprise a first diagnostic engine 104a configured for testing a first type of sample (e.g., a blood sample) and a second diagnostic engine 104b configured for testing a second type of sample (e.g., a urine sample). POC system 100 may comprise any number of diagnostic engines 104a-n for testing any number of different types and combinations of samples. Example diagnostic engines 104a-n include but are not limited to blood gas diagnostic engines, cardiac diagnostic engines, coagulation diagnostic engines, diabetes diagnostic engines, urinalysis diagnostic engines, and blood pressure diagnostic engines.

A blood gas diagnostic engine may be configured to receive a blood sample and to determine one or more characteristics of that blood sample. For example, a blood gas diagnostic engine may be configured to measure one or more of hydrogen ions (pH), partial pressure of carbon dioxide ($pCO_2$) and partial pressure of oxygen ($pO_2$) in a blood sample. The blood gas diagnostic engine may also be configured to measure for the presence and/or concentration of electrolytes and metabolites in the blood sample.

A cardiac diagnostic engine may be configured to receive a sample and measure one or more cardiac health markers. In one embodiment, the cardiac diagnostic engine may receive a blood sample and may be configured to measure one or more of total cholesterol, low-density lipoprotein (LDL) cholesterol, high-density lipoprotein (HDL) cholesterol, triglycerides, non-HDL cholesterol, and high-sensitivity C-reactive protein in the blood sample. In addition, the cardiac diagnostic engine may be configured to test for and/or measure troponin levels in the blood sample.

A coagulation diagnostic engine may be configured to receive a blood sample and to measure one or more blood clotting characteristics. The coagulation diagnostic engine may perform one or more of the following tests: Prothrombin time (PT), Activated Partial Thromboplastin Time (APTT), and Activated Clotting Time (ACT). The coagulation diagnostic engine may apply a chemical membrane to one or more electrodes in a reaction chamber which may create thrombin in the blood sample. An activator may also be present to accelerate the creation of thrombin in the sample.

A diabetes diagnostic engine may be configured to measure one or more diabetes markers in a sample. In one embodiment, the diabetes diagnostic engine may measure a patient's HbA1c levels using a monoclonal antibody addlutination reaction. Additionally or alternatively, the diabetes diagnostic engine may be configured to test Albumin levels in the blood sample using an apolyclonal goat anti-human albumin antiserum and to test the creatinine level of the sample using a Benedict Behre chemical reaction. In some embodiments, IDM 102 may compute a ratio of the Albumin level to the creatinine level in the blood sample.

A urinalysis diagnostic engine may be configured to receive a urine sample and to test for one or more characteristics of the urine sample. Example methodologies may include the use of chromatographic detection pads, colorimetric reagent pads (which may change color depending on the concentration of the analyte in the blood), and optical testing systems in which an image of the urine is put under a microscope and an image recognition algorithm identifies substances in the sample.

As discussed herein, POC system 100 shown in FIG. 1A may comprise any number and any combination of types of different diagnostic engines 104a-n. Each diagnostic engines 104a-n may be configured to receive a test sample, perform a test on the sample, and to send a measured result of that test to IDM 102. Each diagnostic engine 104a-n may also be configured to store one or more measured results in memory 116 of the diagnostic engine.

IDM 102 may be configured to receive as input one or more measured results from one or more of diagnostic engines 104a-n. The measured results may be received, for example, over a communications connection 132 between the one or more diagnostic engines 104a-n and IDM 102. In one embodiment, connection 132 may comprise a wireless connection. For example, connection 132 may comprise a Bluetooth® connection. However, it is understood that connection 132 may be any type of wireless connection, such as a ZigBee connection, a WiFi connection, or the like. In another embodiment, connection 132 may comprise a hard-wired connection. Connection 132 may be made via a USB cable or any other suitable communication cable interface technology. The measured result may comprise one or more values that represent a measured result of the test performed by a diagnostic engine 104a-n. For example, IDM 102 may receive a single value from a diabetes diagnostic engine representing an HbA1c value of a blood sample or may receive multiple values from a cardiac diagnostic engine corresponding to total cholesterol, LDL cholesterol, HDL cholesterol, and triglycerides levels of the blood sample.

IDM 102 may be configured to communicate information to any diagnostic engines 104a-n, such as an instruction to initiate a test, software updates, or changes to the diagnostic engine protocol that may be used by processor 114 of the diagnostic engine 104a-n in generating one or more test results. Control of diagnostic engines 104a-n themselves may be performed by the processors 114 associated with the diagnostic engines 104a-n and/or instructions received from one or more users at diagnostic engines 104a-m.

Processor 106 of IDM 102 may perform a variety of higher-level processing functions of POC system 100. Such higher-level functions may be performed by executing computer-executable instructions (e.g., program code) stored in a computer-readable medium, such as memory 108. IDM 102 may comprise any suitable computing device, such as a tablet computer, laptop computer, desktop computer, personal digital assistant, or other stationary or hand-held computing device.

In some embodiments, processor 106, upon receiving a measured result from a diagnostic engine 104a-n, may be configured to process the measured result so that a calculated result may be presented to a user of POC system 100. For example, IDM 102 may receive one or more values (e.g., measured results) from a diagnostic engine 104a-n. Processor 106 may be configured to determine which values correspond to certain health markers and may determine how to present those values to a user of POC system 100. Processor 106 may be configured to generated calculated results by comparing a received value to one or more other stored or received values and may be configured to compute a ratio of one value to another, such as a triglyceride to HDL cholesterol ratio of a blood sample, in order to generate calculated results.

In some embodiments, processor 106 may be a non-real time processor configured to convert measurements received from a diagnostic engine 104a-n into calculated results capable of being displayed to a user (e.g., via user interface 112). For example, processor 106 may be configured to receive one or more measured results from processor 114 of a diagnostic engine 104a-n upon completion of a test, and process the information as discussed above.

In one embodiment, power for the one or more diagnostic engines 104a-n may be provided by IDM 102. Additionally or alternatively, one or more diagnostic engines 104a-n may provide power for IDM 102.

Memory 108 of IDM 102 may be configured to store a measured result received from any of diagnostic engines 104a-n and/or one or more calculated results generated by IDM 102. Memory 108 may be configured to store any number of measured or calculated results before they are deleted (e.g., one thousand results) or may be configured to store the measured or calculated results for a determined period of time (e.g., one year). Memory 108 may further store information associated with one or more patients as described previously. For example, memory 108 may store patient information such as an identifier associated with the patient, patient last name, patient first name, patient gender, and patient date of birth.

FIG. 2A illustrates an example data structure 200, such as a database or lookup table, of patient information that may be stored in memory 108. With reference to FIG. 2A, data structure 200 may associate patient information such as patient last name, patient first name, patient date of birth, patient address, etc., with a patient ID. In some embodiments, memory 108 may store patient test results (not shown) along with the patient information so that they may be retrieved at a later date.

Figure 2C:
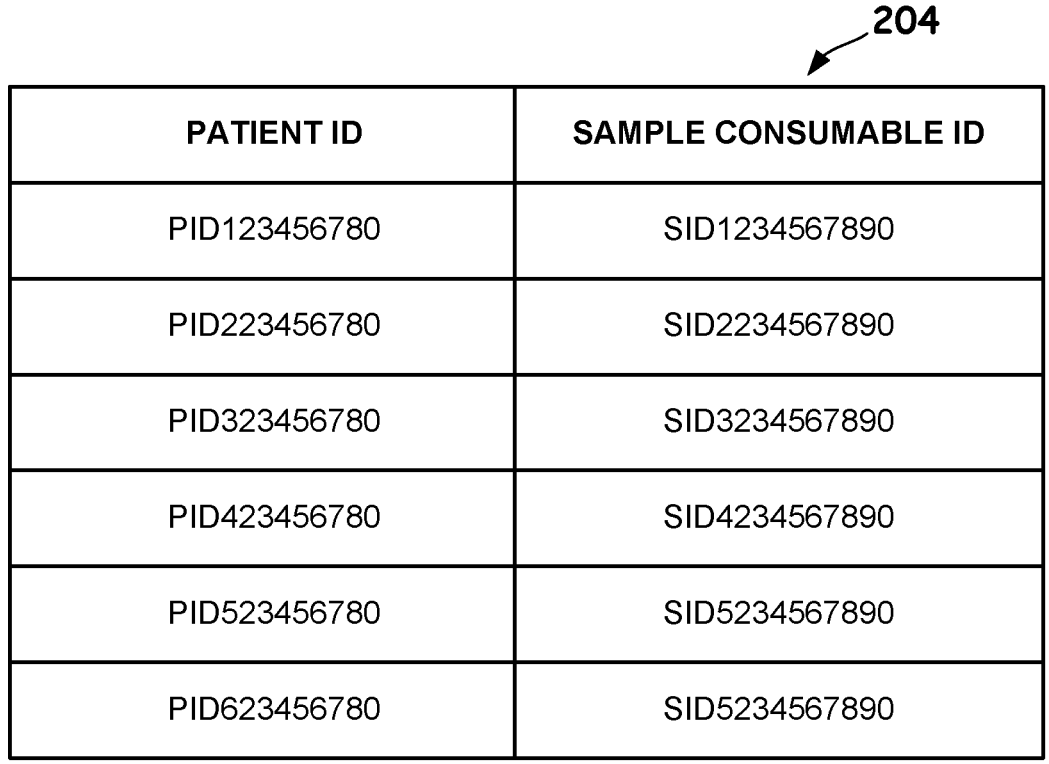
FIG. 2C illustrates an example data structure in which patient ID information may be linked with diagnostic consumable ID information in accordance with embodiments of the disclosure.

As will be described further below, memory 108 also may store diagnostic consumable information, and may link patient ID information with diagnostic consumable ID information prior to sample collection (e.g., just prior to sample collection using the diagnostic consumable). For example, FIG. 2B illustrates an example data structure 204, such as a database or lookup table, of diagnostic consumable information, such as diagnostic consumable ID, the test to be performed on/with the diagnostic consumable, etc., that may be stored in memory 108. FIG. 2C illustrates an example data structure 206, such as a database or lookup table, in which patient ID information is linked with diagnostic consumable ID information, and that may be stored in memory 108 (e.g., prior to sample collection).

Operation of POC system 100 of FIG. 1A is now described with reference to FIGS. 1A-4P, in which FIG. 3A illustrates an example method 300 for collecting patient ID information and diagnostic consumable ID information, and linking patient ID information and diagnostic consumable ID information within IDM 102 in accordance with embodiments disclosed herein; FIG. 3B illustrates an example method 310 for ensuring patient ID information and diagnostic consumable ID information are linked within IDM 102 before allowing testing with any diagnostic engine 104*a-n* in accordance with embodiments disclosed herein; and FIGS. 4A-4P illustrate example display screen layouts during operation of user interface 112 of IDM 102 within POC system 100 of FIG. 1A in accordance with embodiments disclosed herein.

With reference to FIG. 3A, method 300 may be performed by POC system 100 and includes obtaining ID information for a patient (Block 302), obtaining ID information for a diagnostic consumable (Block 304), and linking patient ID information with diagnostic consumable ID information (Block 306). In some embodiments, method 300 may be performed immediately prior to a sample being collected from a patient (e.g., prior to a blood draw, finger prick, urine collection, etc.).

Patient ID information may be entered into IDM 102 and stored in memory 108. In some embodiments, patient ID information may be entered manually through user interface 112 of IDM 102. In other embodiments, camera 110 of IDM 102 may scan patient ID information into IDM 102 for storage into memory 108, such as by scanning a barcode on paperwork or a wrist band associated with the patient. In one or more embodiments, a barcode may be scanned and used to lookup patient information previously stored on a server (e.g., for storage into memory 108 of IDM 102). An example wrist band 134 is shown in FIG. 1A that includes a barcode 136 with encoded patient ID information. In some embodiments, the barcode 136 of wrist band 134 may be scanned by camera 110 or another imaging device to obtain patient ID information for storage in memory 108 of IDM 102.

Example patient ID information may include the patient's name, date of birth, gender, mailing address, email address, allergies, medical history or the like. Example patient information, stored in a database or lookup table in memory 108, is shown in FIG. 2A.

Diagnostic consumable ID information similarly may be entered into IDM 102 and stored in memory 108. In some embodiments, diagnostic consumable ID information may be entered manually through user interface 112 of IDM 102. In other embodiments, camera 110 of IDM 102 may scan diagnostic consumable ID information into IDM 102 for storage into memory 108, such as by scanning a barcode on a sample cartridge, urine (sample) cup, test strip or other diagnostic consumable. An example diagnostic consumable 138 is shown in FIG. 1A that includes a barcode 140 encoded with diagnostic consumable ID information. In some embodiments, the barcode 140 of diagnostic consumable 138 may be scanned by camera 110 or another imaging device to obtain diagnostic consumable ID information for storage in memory 108 of IDM 102.

Example diagnostic consumable ID information includes a diagnostic consumable ID number, the type of test to be performed on the diagnostic consumable, the time the diagnostic consumable ID was scanned, calibration information, expiration date, lot number, or the like. Example diagnostic consumable information, stored in a database or lookup table in memory 108, is shown in FIG. 2B.

Within IDM 102, patient ID information and diagnostic consumable ID information may be linked. For example, patient ID information and diagnostic consumable ID information may be stored together in memory 108, such as in a database or lookup table (e.g., as shown in FIG. 2C). Patient ID information and diagnostic consumable ID information may be otherwise linked. Permanently linking patient ID information and diagnostic consumable ID information within IDM 102 may help ensure that a diagnostic test performed on a diagnostic consumable is always associated with the correct patient as described below.

In a busy point of care environment, many patients may be providing samples for testing using many different diagnostic engines. Once a patient provides a sample using a diagnostic consumable, the sample (in the form of a diagnostic consumable) may be transferred to a diagnostic engine along with other patient samples. In some cases, a large queue of samples (e.g., diagnostic consumables) may be present at one or more diagnostic engines. Having each diagnostic consumable linked with a patient within IDM 102 at/near the time of sample collection helps ensure test results are associated with the correct patient(s).

With reference to FIG. 3B, method 310 may be performed by POC system 100 once sample testing is to be performed, such as after sample collection. For example, once a sample has been collected using a diagnostic consumable, method 310 may include obtaining ID information for the diagnostic consumable having the sample to be tested (Block 312), and confirming the diagnostic consumable is valid (Block 314). For example, a barcode scanner, such as scanner 118 of one of diagnostic engines 104*a-n* of FIG. 1A, may be used to scan a barcode on the diagnostic consumable to determine its diagnostic consumable ID information. In some embodiments, inserting a diagnostic consumable into a diagnostic engine for testing may cause a barcode on the diagnostic consumable to be scanned. Alternatively, a separate barcode scanner that is part of or separate from the diagnostic engine may be used to obtain diagnostic consumable ID information. The diagnostic engine may then provide the scanned diagnostic consumable ID information to IDM 102.

Once IDM 102 receives ID information for a diagnostic consumable, IDM 102 may determine if the diagnostic consumable is valid. For example, IDM 102 may determine if the ID number for the diagnostic consumable is a valid ID number, corresponds to a proper type of diagnostic consumable for the diagnostic engine being used, etc. If not, method 310 ends (Block 316); otherwise method 310 includes determining if the diagnostic consumable ID information is linked with patient ID information within IDM 102 (Block 318). For example, IDM 102 may access memory 108 to determine if the diagnostic consumable ID information is linked with patient ID information. If not, the diagnostic engine may be prevented (or otherwise restricted or limited) from testing the sample collected with the diagnostic consumable and method 310 ends (Block 316); otherwise, if the diagnostic consumable ID information is linked or otherwise associated with patient ID information, IDM 102 allows the diagnostic engine to perform testing on the sample collected with the diagnostic consumable (Block 320). For example, IDM 102 may issue an instruction to the diagnostic engine indicating that the diagnostic engine should commence testing. Following testing, test results from the diagnostic engine may be communicated to IDM 102 and/or stored with patient ID information as described below.

In some embodiments, when method 310 ends at block 316, either due to an invalid diagnostic consumable being detected or a diagnostic consumable not being linked with a patient in IDM 102, the diagnostic engine is prevented or otherwise restricted from performing any testing on the sample collected with the diagnostic consumable. For example, IDM 102 may employ user interface 112 to alert an operator that an error has occurred, to flag the invalid or unlinked diagnostic consumable, etc.

FIGS. 4A-4P illustrate example display screen layouts 400*a-p* displayed by user interface 112 of IDM 102 of FIG. 1A during testing of a sample collected with a diagnostic consumable in accordance with embodiments provided herein. Display screens layouts 400*a-p* of FIGS. 4A-4P are merely examples. Other screen layouts, icons, information, order of screen layouts, content and/or the like may be employed. Computer program code and/or instructions for producing the display screen layouts 400*a-p* of FIGS. 4A-4P, receiving input from a user of IDM 102, communicating information between IDM 102 and diagnostic engines 104*a-n*, etc., may be stored in memory 108 and executed by processor 106 of IDM 102, for example.

With reference to FIG. 4A, an initial screen layout 400*a* indicates that IDM 102 is operational and ready to receive input. After selection of the Login icon by a user, user interface 112 displays the screen layout 400*b* shown in FIG. 4B at which a user may enter and/or otherwise provide user authentication information to proceed with testing. Example user authentication information may include an operator ID and password, information contained within an employee badge with a scannable barcode, information contained within a radio-frequency identification (RFID) tag, two-factor authentication information such as a password and a one-time code sent via text, email, or a smart phone application, etc. In some embodiments, a user may input operator ID information by scanning a barcode (e.g., on a name tag, wrist band, etc.). For example, camera 110 of IDM 102 or another imaging device may be employed to scan a barcode to provide operator ID information to IDM 102. Alternatively, operator ID information may be entered manually (e.g., via a keyboard, touch screen, or the like).

Once a valid operator ID has been provided to and/or authenticated by IDM 102, IDM 102 may be used to collect patient ID information (FIG. 4C) that is associated with a diagnostic consumable (FIG. 4D). As shown in display screen layout 400*c* FIG. 4C, patient ID information may be manually entered into IDM 102, scanned using camera 110 or another imaging device, or otherwise provided to IDM 102. In some embodiments, patient information may be obtained from a previously stored list or database of patient information (e.g., data structure 200 of FIG. 2A). Patient information may be stored in memory 108 of IDM 102, for example, such as in data structure 200 (FIG. 2A).

Once patient ID information is provided, diagnostic consumable ID information (e.g., sample ID information) may be obtained by IDM 102 as shown in display screen layout 400*d* of FIG. 4D. Diagnostic consumable ID information may be manually entered into IDM 102, scanned using camera 110 or another imaging device, or otherwise provided to IDM 102. In some embodiments, each diagnostic consumable such as a sample cartridge in which blood is stored, a urine cup, a test strip such as a urine or lateral flow strip, etc., may be provided with a scannable barcode such as barcode 140 of diagnostic consumable 138 of FIG. 1A. In some embodiments, diagnostic consumable ID information may be stored in memory 108 of IDM 102, such as in data structure 202 of FIG. 2B. As described previously, IDM 102 may link patient ID information with diagnostic consumable ID information. For example, patient ID information and diagnostic consumable ID information may be stored in memory 108 of IDM 102, such as in data structure 204 of FIG. 2C.

Once patient ID information and diagnostic consumable ID information is linked within IDM 102 for a patient and a diagnostic consumable, a sample may be collected from the patient using the diagnostic consumable and the diagnostic consumable may be sent for testing by one of diagnostic engines 104*a-n*. For example, a urine, blood, plasma, saliva, cerebrospinal fluid, pleural fluid, nasopharyngeal, or other sample.

Once a sample is collected with a diagnostic consumable and arrives at a diagnostic engine for testing, the diagnostic consumable is scanned at the diagnostic engine. In some embodiments, IDM 102 may use user interface 112 to instruct a technician to scan the diagnostic consumable as shown in display screen layout 400*e* of FIG. 4E. For example, a barcode reader within a diagnostic engine (e.g., scanner 118 of diagnostic engines 104*a-n* in FIG. 1A) may scan the diagnostic consumable when the diagnostic consumable is inserted into the diagnostic engine. Alternatively, another imaging device internal or external to the diagnostic engine may be employed to scan a barcode on the diagnostic consumable. In some embodiments, diagnostic consumable ID information may be manually entered via a keyboard, touch screen, etc. Scanned (or otherwise obtained) diagnostic consumable ID information is then communicated by the diagnostic engine to IDM 102, such as via connection 132 (FIG. 1A).

As previously discussed with referenced to FIG. 3B, IDM 102 may determine whether diagnostic consumable ID information provided by a diagnostic engine is linked with a patient (e.g., patient ID information) within IDM 102. If so, IDM 102 may allow the diagnostic engine to perform testing on a sample collected using the diagnostic consumable. However, if the diagnostic consumable ID provided by the diagnostic engine is not linked with a patient (e.g., patient ID information) within IDM 102, IDM 102 may prevent or otherwise restrict the diagnostic engine from performing testing on the sample collected using the diagnostic consumable. For example, IDM 102 and/or the diagnostic engine may issue a warning or alarm, eject the diagnostic consumable from the diagnostic engine, or the like.

Figure 4E:
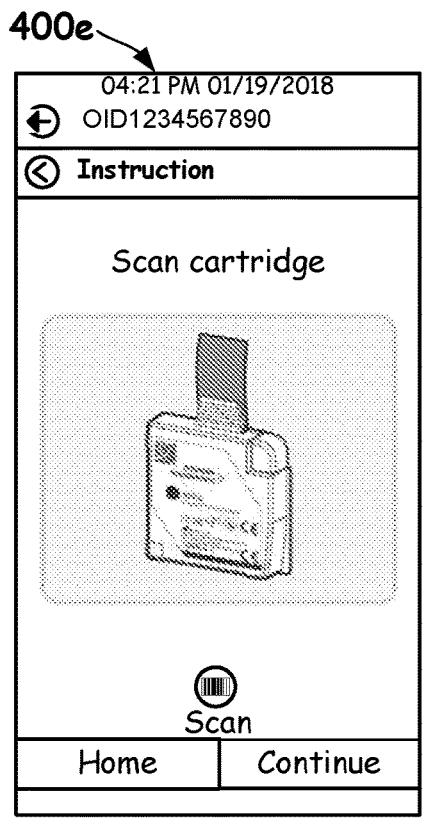
FIGS. 4A-4P illustrate example display screen layouts during operation of the user interface of the instrument data manager of the point of care system of FIG. 1A in accordance with embodiments disclosed herein.
Figure 4F:
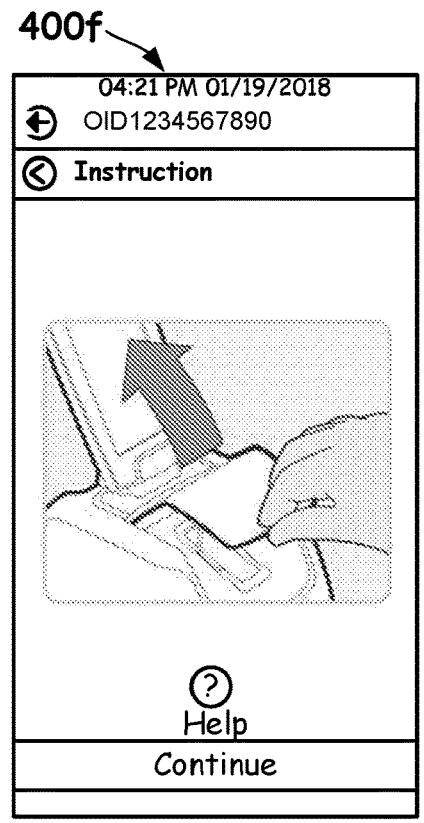
Figure 4G:
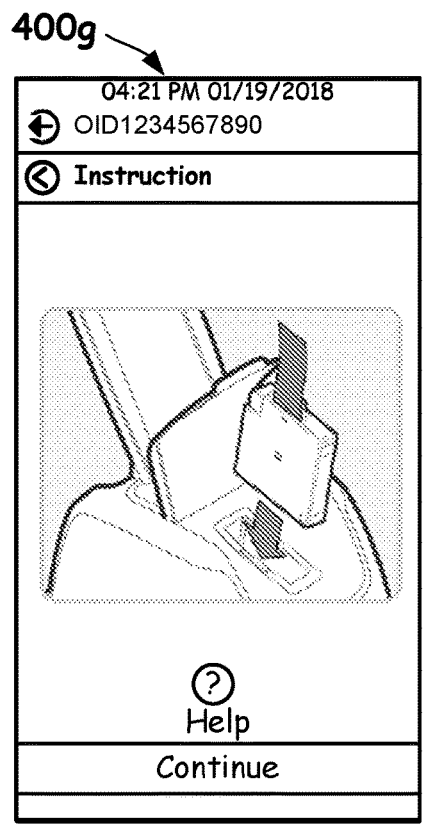
Figure 4H:
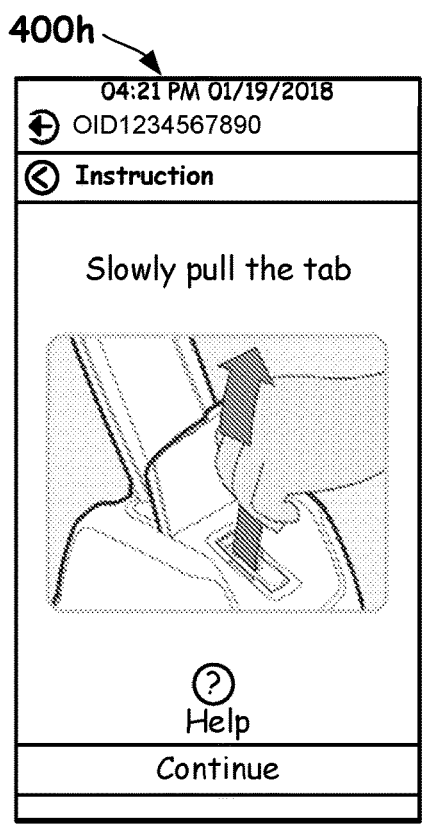
Figure 4I:
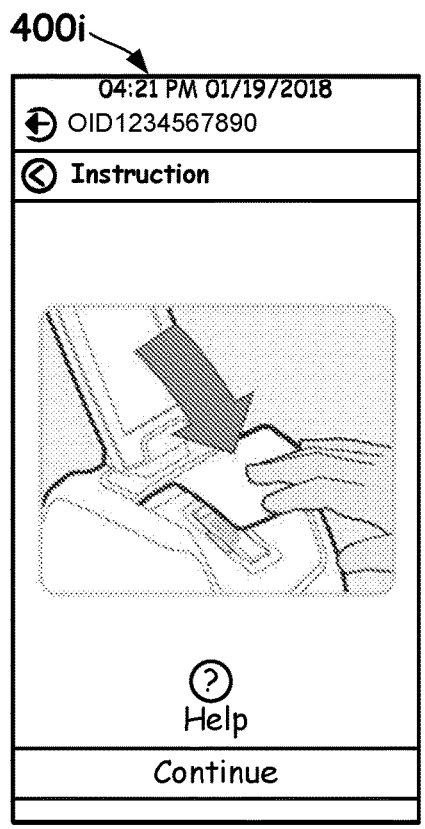

Assuming the diagnostic consumable is linked with a patient within IDM 102, user interface 112 may instruct the technician to load the diagnostic consumable into the diagnostic engine as shown in example display screen layouts 400*f* and 400*g* of FIGS. 4F and 4G, respectively. In some embodiments, user interface 112 may instruct the technician to prepare the diagnostic consumable for testing, such as by removing a sealing tab, cover, or the like, as shown in display screen layout 400*h* of FIG. 4H, and/or prepare the diagnostic engine for testing, such as by closing a lid or cover the diagnostic engine, as shown in display screen layout 400*i* of FIG. 4I.

Figure 4J:
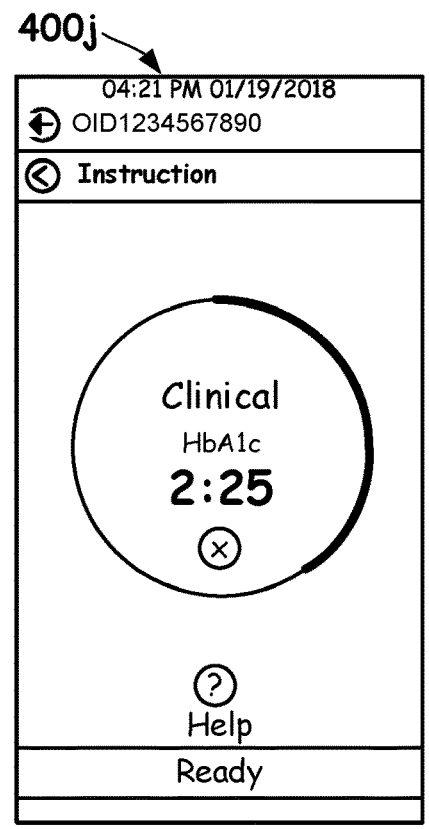
Figure 4K:
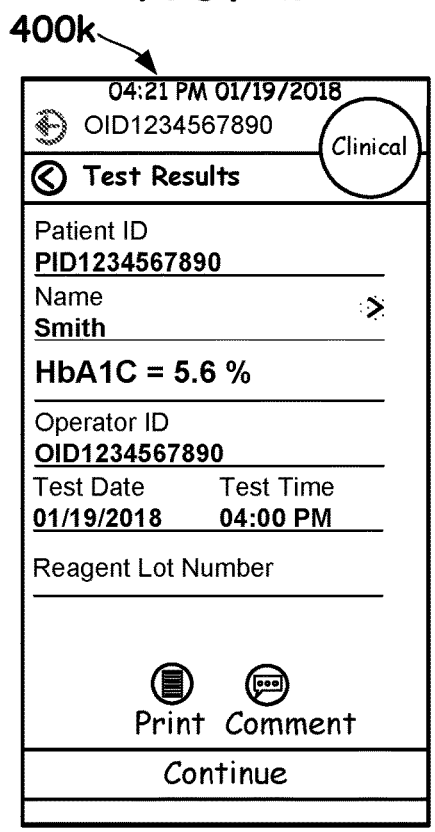

Once the diagnostic consumable is loaded within the diagnostic engine, testing may begin as shown in display screen layout 400*j* of FIG. 4J. For example, either IDM 102 or the diagnostic engine being used may initiate testing. In some embodiments, user interface 112 may display the type of test being performed (e.g., an HbA1C measurement in FIG. 4J), how long the test has been running, how much time is remaining, etc.

Once testing is complete, measured results may be communicated from the diagnostic engine to IDM 102. In some embodiments, IDM 102 may receive one or more measured results from a diagnostic engine, process the measured results to generate calculated results, and present the calculated results and other information such as patient information via user interface 112 as shown in display screen layout 400k of FIG. 4K. Alternatively, the diagnostic engine may provide calculated results to IDM 102 for display via user interface 112. In some embodiments, user interface 112 may allow a user to print results, comment on results, etc.

Figure 4L:
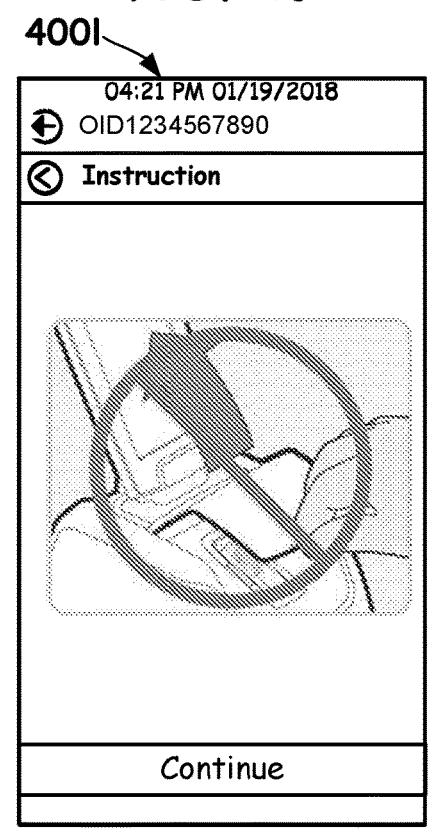
Figure 4M:
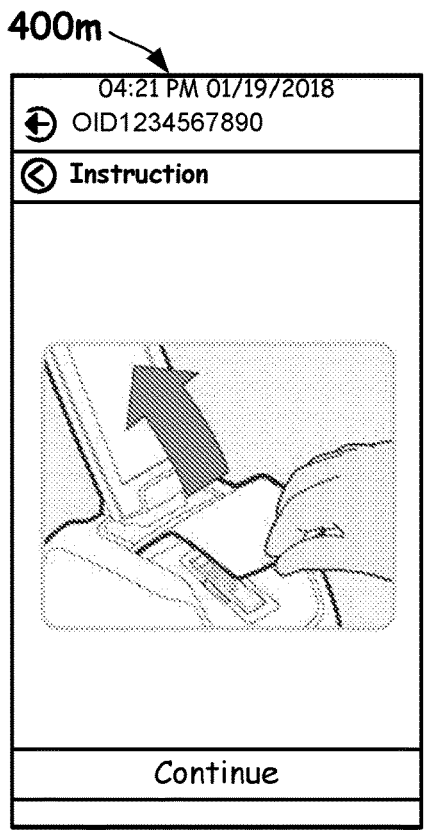
Figure 4N:
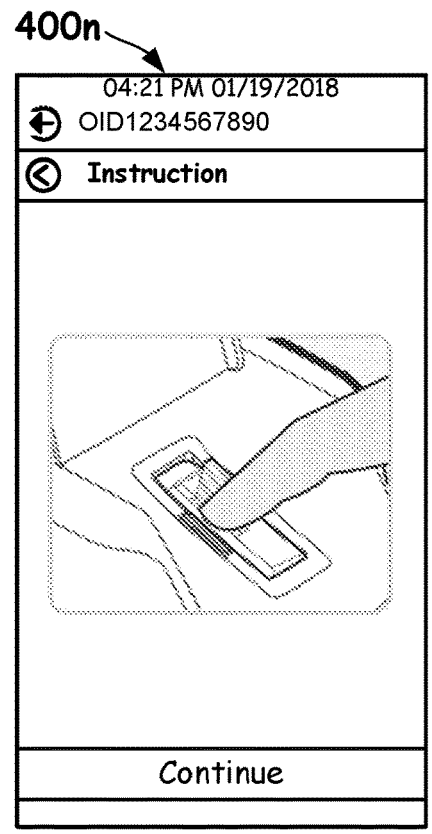
Figure 4O:
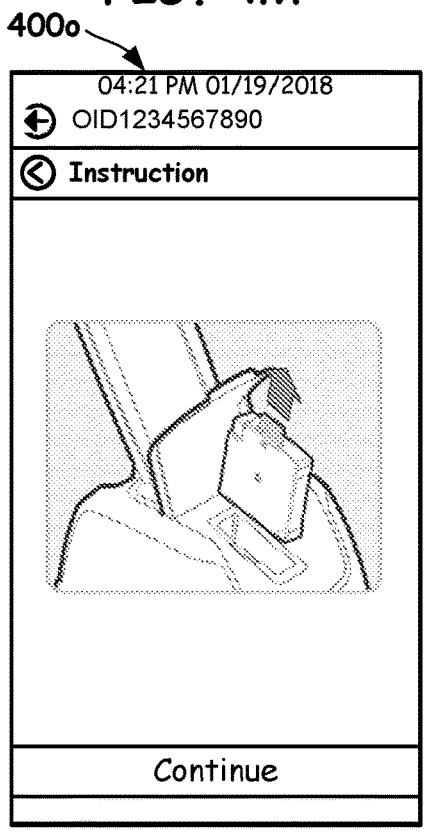
Figure 4P:
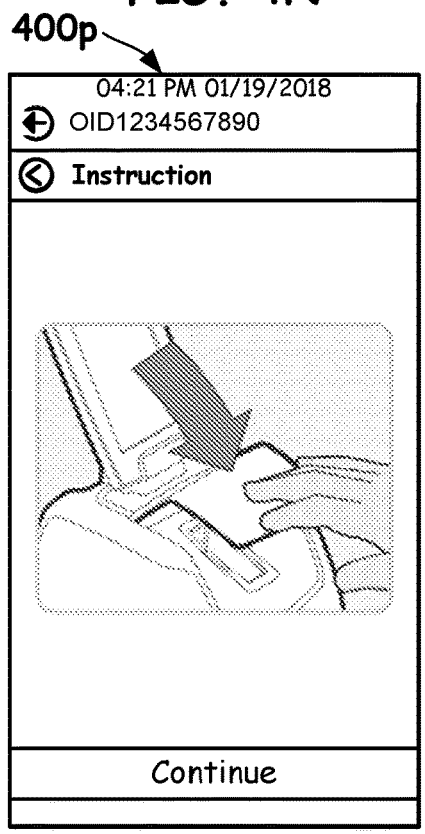

If the diagnostic consumable is not ready to be removed from the diagnostic engine in which it is tested (e.g., because the diagnostic consumable is at an elevated temperature or for some other reason), user interface 112 may indicate that the diagnostic consumable should not be removed, as shown in display screen layout 4l of FIG. 4L. Likewise, if the diagnostic consumable is ready to be removed from the diagnostic engine in which it is tested, user interface 112 may indicate that the diagnostic consumable may be removed, as shown in display screen layout 400m of FIG. 4M. In some embodiments, user interface 112 may provide step-by-step instructions for removing the diagnostic consumable, such as raising the lid or cover the diagnostic engine (FIG. 4M), pressing a release or other mechanism used to secure the diagnostic consumable within the diagnostic engine (FIG. 4N), retrieving the diagnostic consumable from the diagnostic engine (FIG. 4O), and/or closing the lid or cover of the diagnostic engine (FIG. 4P). (See display screen layouts 400m, 400n, 400o and 400p, of FIGS. 4M, 4N, 4O and 4P, respectively, for example.) Other, fewer and/or different user interface screens, layouts, information, etc., may be employed to implement the various steps of methods 300 and/or 310 of FIGS. 3A and/or 3B.

By linking patient ID information and diagnostic consumable ID information at the time the sample is taken, and then confirming that any diagnostic consumable having a sample to be tested is linked with a patient within the IDM prior to testing with a diagnostic engine, test results are properly associated with the correct patient(s).

It is understood that POC system 100 and any of the components described herein may be part of an "open system." For example, IDM 102 may be configured to connect and communicate with diagnostic engines 104a-n from a variety of manufacturers. IDM 102 may be configurable to download or install new software that enables IDM 102 to communicate with the variety of diagnostic engines. In some embodiments, user interface 112 may comprise an icon that enables one or more new diagnostic engines to be added to IDM 102. In one example, a given diagnostic engine may only be controllable by a single IDM 102. In another example, a diagnostic engine may be controllable by a plurality of IDMs 102.

In one example, both a diagnostic engine 104a-n and IDM 102 may be developed by the same manufacturer. In another example, a diagnostic engine 104a-n may be developed by an external partner of the manufacturer that utilizes both of the diagnostic engines user interface and world interfaces. IDM software may need to be updated to accommodate such a diagnostic engine. In another example, a diagnostic engine 104a-n may be developed by an external partner of the manufacturer that utilizes only the world interface of the diagnostic engine but not the user interface. In another example, a diagnostic engine 104a-n may be a virtual engine that works in cooperation with the hardware and software of other external devices. In an example, this could be a blood pressure monitor that allows IDM 102 to combine results from a blood pressure monitor with other measured or calculated results to generate new calculated results. In another example, diagnostic engine 104a-n may be a virtual engine that comprises only an application that can obtain and manipulate data. For example, the diagnostic engine may submit a questionnaire to a patient, measure ambient temperature, humidity, etc. These results may be combined with other measured or calculated results to generate new calculated results.

In some embodiments, diagnostic engines may not include a user interface. In such embodiments, communication to/from a diagnostic engine may be performed through user interface 112 of IDM 102, for example.

The foregoing description discloses only example embodiments of the invention; modifications of the above disclosed apparatus and method which fall within the scope of the invention will be readily apparent to those of ordinary skill in the art. Accordingly, while the present invention has been disclosed in connection with the example embodiments thereof, it should be understood that other embodiments may fall within the spirit and scope of the invention, as defined by the following claims.

ILLUSTRATIVE EMBODIMENTS

1. A method of providing point of care diagnostic testing using a diagnostic engine, comprising:
    employing an instrument data manager (IDM) to:
    obtain identification (ID) information of a patient for which a test is to be performed using the diagnostic engine;
    obtain ID information of a diagnostic consumable to be used to collect a sample from the patient;
    link the obtained patient ID information with the obtained diagnostic consumable ID information; and
    restricting testing using the diagnostic engine by:
    prior to performing a test on a sample collected with a diagnostic consumable, determining ID information of the diagnostic consumable at the diagnostic engine;
    determining whether the diagnostic consumable is linked with patient ID information within the IDM; and
    if the diagnostic consumable is linked with patient ID information within the IDM, allowing the diagnostic engine to perform a test on the sample collected with the diagnostic consumable.

2. The method of claim 1, wherein at least one of obtaining ID information of a patient and obtaining ID information of a diagnostic consumable includes using the IDM to scan a barcode.

3. The method of claim 2, where using the IDM to scan a barcode includes employing a camera of the IDM to determine barcode information.

4. The method of claim 1, wherein prior to performing a test on a sample collected with a diagnostic consumable with the diagnostic engine, determining ID information for the diagnostic consumable includes using the diagnostic engine to scan a barcode of the diagnostic consumable to determine diagnostic consumable ID information for the diagnostic consumable.

5. The method of claim 4, wherein using the diagnostic engine to scan a barcode of the diagnostic consumable includes scanning a barcode of the diagnostic consumable when the diagnostic consumable is inserted into the diagnostic engine.

6. The method of claim 4, wherein the diagnostic engine includes a barcode scanner that allows an operator to scan a barcode of a diagnostic consumable before the diagnostic consumable is inserted into the diagnostic engine.

7. The method of claim 1, wherein the IDM is configured to communicate with the diagnostic engine via wireless communications.

8. The method of claim 1, wherein the diagnostic engine is configured to analyze samples collected with diagnostic consumables that include a urine sample cup or a sample cartridge.

9. The method of claim 1, wherein the diagnostic engine does not include a user interface.

10. The method of claim 1, wherein the IDM is configured to:
interface with a plurality of diagnostic engines; and for two or more of the plurality of diagnostic engines, prior to testing a sample collected with a diagnostic consumable using any of the two or more of the plurality of diagnostic engines, confirm at the diagnostic engine that the diagnostic consumable is linked with patient ID information prior to allowing testing with the diagnostic engine.

11. The method of claim 10, wherein the plurality of diagnostic engines comprise at least one of a blood gas diagnostic engine, a cardiac diagnostic engine, a coagulation diagnostic engine, a diabetes diagnostic engine, and a urinalysis diagnostic engine.

12. A method of providing point of care diagnostic testing using a diagnostic engine, comprising:
employing an instrument data manager (IDM) to obtain identification (ID) information of a patient for which a test is to be performed using the diagnostic engine;
employing the IDM to scan ID information of a diagnostic consumable to be used to collect a sample from the patient;
linking the patient ID information with the diagnostic consumable ID information within the IDM; and
prior to performing a test on a sample collected with a diagnostic consumable:
scanning ID information of the diagnostic consumable at the diagnostic engine;
communicating the scanned ID information to the IDM;
confirming that the diagnostic consumable is linked with the patient ID information within the IDM; and
if the diagnostic consumable is linked with the patient ID information within the IDM, directing the diagnostic engine to perform a test on the sample collected with the diagnostic consumable.

13. The method of claim 12, further comprising:
if the diagnostic consumable is not linked with patient ID information within the IDM, preventing the diagnostic engine from performing a test on the sample collected with the diagnostic consumable.

14. The method of claim 12, wherein at least one of obtaining ID information of a patient and obtaining ID information of a diagnostic consumable includes using the IDM to scan a barcode.

15. An instrument data manager (IDM) configured to control operation of a plurality of diagnostic engines comprising:
a display;
a processor coupled to the display; and
a memory coupled to the processor, the memory having stored therein a plurality of computer executable instructions that, when executed by the processor, cause the IDM to:
provide a user interface through which the IDM obtains identification (ID) information for patients and ID information for diagnostic consumables;
after obtaining patient ID information and diagnostic consumable ID information with the user interface, link the diagnostic consumable ID information with the patient ID information;
receive diagnostic consumable ID information from the plurality of diagnostic engines; and
prevent testing of samples collected with diagnostic consumables at one or more of the plurality of diagnostic engines if diagnostic consumable ID information received from the one or more of the plurality of diagnostic engines is not linked to patient ID information within the IDM.

16. The IDM of claim 15, wherein the memory includes computer executable instructions that direct the processor to link patient ID information and diagnostic consumable ID information in a database.

17. The IDM of claim 15, where the memory includes computer executable instructions that initiate testing by a diagnostic engine if diagnostic consumable ID information received from the diagnostic engine is linked to patient ID information with the IDM.

18. A method performed by an instrument data manager (IDM) in communication with a plurality of diagnostic engines, the IDM being configured to communicate with each of the plurality of diagnostic engines to enable a plurality of tests to be performed on a plurality of samples using the plurality of diagnostic engines, the method comprising:
obtaining, via a user interface of the IDM, identification (ID) information of a patient for which a test is to be performed;
obtaining, via the user interface of the IDM, ID information of a diagnostic consumable to be used to collect a sample from the patient;
linking, within the IDM, the obtained patient ID information with the obtained diagnostic consumable ID information; and
restricting testing using the plurality of diagnostic engines by:
prior to allowing performance of a test on a sample collected with a diagnostic consumable within any of the plurality of the diagnostic engines, receiving ID information of the diagnostic consumable from a diagnostic engine;
determining whether the diagnostic consumable ID information is linked with patient ID information within the IDM; and
if the diagnostic consumable ID information is linked with patient ID information within the IDM, allowing the diagnostic engine to perform a test on the sample collected with the diagnostic consumable.

19. The method of claim 18, further comprising:
if the diagnostic consumable is not linked with patient ID information within the IDM, preventing the diagnostic engine from performing a test on the sample collected with the diagnostic consumable.

20. A point of care system comprising:
a diagnostic engine configured to perform a test on a sample and to generate a measured result based on the test on the sample; and
an instrument data manager (IDM) in electronic communication with the diagnostic engine, the IDM being configured to:
obtain identification (ID) information of a patient for which a test is to be performed using the diagnostic engine;

obtain ID information of a diagnostic consumable to be used to collect a sample from the patient;

link the obtained patient ID information with the obtained diagnostic consumable ID information; and restrict testing using the diagnostic engine by:

prior to performing a test on a sample collected with a diagnostic consumable, determine ID information of the diagnostic consumable at the diagnostic engine;

determine whether the diagnostic consumable is linked with patient ID information within the IDM; and if the diagnostic consumable is linked with patient ID information within the IDM, allow the diagnostic engine to perform a test on the sample collected with the diagnostic consumable.

21. The point of care system of claim 20, wherein the IDM is configured to:

if the diagnostic consumable is not linked with patient ID information within the IDM, prevent the diagnostic engine from performing a test on the sample collected with the diagnostic consumable.

22. The point of care system of claim 20, wherein the IDM is configured to scan a barcode to determine at least one of the patient ID information and the diagnostic consumable ID information.

23. The point of care system of claim 22, wherein the IDM is configured to employ a camera of the IDM to scan at least one of the patient ID information and the diagnostic consumable ID information.

24. The point of care system of claim 20, wherein the diagnostic engine is configured to scan barcodes of diagnostic consumables to determine diagnostic consumable ID information for each diagnostic consumable and communicate sample ID information to the IDM.

25. The point of care system of claim 24, wherein the diagnostic engine is configured to scan a barcode of a diagnostic consumable when the diagnostic consumable is inserted into the diagnostic engine.

26. The point of care system of claim 24, wherein the diagnostic engine includes a barcode scanner that allows an operator to scan a barcode of a diagnostic consumable before the diagnostic consumable is inserted into the diagnostic engine.

27. The point of care system of claim 20, wherein the IDM is configured to communicate with the diagnostic engine via wireless communications.

28. The point of care system of claim 20, wherein the diagnostic engine is configured to analyze samples collected with diagnostic consumables that include a urine sample cup or a sample cartridge.

29. The point of care system of claim 20, wherein the diagnostic engine does not include a user interface.

30. The point of care system of claim 20, wherein the IDM is configured to:

interface with a plurality of diagnostic engines; and for each diagnostic engine, prior to testing a sample collected with a diagnostic consumable, confirm at the diagnostic engine that the diagnostic consumable is linked with patient ID information prior to allowing testing with the diagnostic engine.

31. The point of care system of claim 30, wherein the plurality of diagnostic engines comprise at least one of a blood gas diagnostic engine, a cardiac diagnostic engine, a coagulation diagnostic engine, a diabetes diagnostic engine, and a urinalysis diagnostic engine.

What is claimed is:

1. A point of care system comprising:

an instrument data manager (IDM) configured to communicate with a diagnostic engine, the IDM comprising a user interface, a camera, a processor, and a memory having computer executable instructions stored therein, the IDM configured via the computer executable instructions to:

receive via the user interface or the camera identification (ID) information of a patient for which a test is to be performed using the diagnostic engine;

receive via the user interface or the camera ID information of a diagnostic consumable to be used to collect a sample from the patient;

link via a data structure stored in the memory the received patient ID information with the received diagnostic consumable ID information;

receive from the diagnostic engine, prior to performing a test on a sample collected with a diagnostic consumable received at the diagnostic engine, ID information of the diagnostic consumable received at the diagnostic engine;

determine via the processor whether the diagnostic consumable received at the diagnostic engine is linked with patient ID information stored in the memory; and if the diagnostic consumable received at the diagnostic engine is not linked with patient ID information stored in the memory, transmit instructions to the diagnostic engine to prevent the diagnostic engine from performing a test on the sample collected with the diagnostic consumable received at the diagnostic engine.

2. The point of care system of claim 1, wherein the IDM is further configured to:

if the diagnostic consumable is linked with patient ID information within the IDM, transmit instructions to the diagnostic engine to perform a test on the sample collected with the diagnostic consumable.

3. The point of care system of claim 1, wherein the IDM is configured via the camera to scan a barcode to determine at least one of the patient ID information and the diagnostic consumable ID information.

4. The point of care system of claim 1, wherein the user interface includes one or more of a display screen, a touch panel or screen, an audio speaker, and a microphone.

5. The point of care system of claim 1, further comprising the diagnostic engine, wherein the diagnostic engine is configured to perform a test on a sample and to generate a measured result based on the test on the sample.

6. The point of care system of claim 5, wherein the diagnostic engine is configured to scan barcodes of diagnostic consumables to determine diagnostic consumable ID information for each diagnostic consumable and communicate diagnostic consumable ID information to the IDM.

7. The point of care system of claim 5, wherein the diagnostic engine is configured to scan a barcode of a diagnostic consumable when the diagnostic consumable is inserted into the diagnostic engine.

8. The point of care system of claim 5, wherein the diagnostic engine includes a barcode scanner that allows an operator to scan a barcode of a diagnostic consumable before the diagnostic consumable is inserted into the diagnostic engine.

9. The point of care system of claim 5, wherein the diagnostic engine is configured to analyze samples collected with diagnostic consumables that include a urine sample cup or a sample cartridge.

10. The point of care system of claim 5, wherein the diagnostic engine does not include a user interface.

11. The point of care system of claim 1, wherein the IDM is configured to communicate with the diagnostic engine via wireless communications.

12. The point of care system of claim 1, wherein the IDM is configured to:
interface with a plurality of diagnostic engines; and
for two or more of the plurality of diagnostic engines, prior to testing a sample collected with a diagnostic consumable using any of the two or more of the plurality of diagnostic engines, confirm at the diagnostic engine that the diagnostic consumable is linked with patient ID information prior to allowing testing with the diagnostic engine.

13. The point of care system of claim 12, wherein the plurality of diagnostic engines comprises at least one of a blood gas diagnostic engine, a cardiac diagnostic engine, a coagulation diagnostic engine, a diabetes diagnostic engine, and a urinalysis diagnostic engine.

14. A method of providing point of care diagnostic testing using a diagnostic engine and employing an instrument data manager (IDM) comprising a user interface, a camera, a processor, and a memory having computer executable instructions stored therein, the IDM configured via the computer executable instructions to perform the method comprising:
receiving via the user interface or the camera identification (ID) information of a patient for which a test is to be performed using the diagnostic engine;
receiving via the user interface or the camera ID information of a diagnostic consumable to be used to collect a sample from the patient;
linking via a data structure stored in the memory the received patient ID information with the received diagnostic consumable ID information;
prior to performing a test on a sample collected with a diagnostic consumable, receiving from the diagnostic engine ID information of the diagnostic consumable at the diagnostic engine;
determining via the processor whether the diagnostic consumable is linked with patient ID information stored in the memory; and
if the diagnostic consumable is not linked with patient ID information stored in the memory, transmitting instructions to the diagnostic engine to prevent the diagnostic engine from performing a test on the sample collected with the diagnostic consumable.

15. The method of claim 14, further comprising:
if the diagnostic consumable is linked with patient ID information stored in the memory, transmitting instructions to the diagnostic engine to perform a test on the sample collected with the diagnostic consumable.

16. The method of claim 14, wherein at least one of the receiving ID information of a patient and the receiving ID information of a diagnostic consumable includes using the IDM to scan a barcode.

17. A method of providing point of care diagnostic testing using a diagnostic engine, comprising:
receiving via a user interface or a camera identification (ID) information of a patient for which a test is to be performed using the diagnostic engine;
receiving via a user interface or a camera ID information of a diagnostic consumable to be used to collect a sample from the patient;
linking via a data structure stored in a memory the patient ID information with the diagnostic consumable ID information; and
prior to performing a test on a sample collected with the diagnostic consumable with the diagnostic engine:
scanning via a scanner at the diagnostic engine ID information of the diagnostic consumable received at the diagnostic engine;
determining via a processor whether the diagnostic consumable is linked via the data structure with the patient ID information; and
if the diagnostic consumable is not linked with the patient ID information, transmitting instructions to the diagnostic engine to prevent the diagnostic engine from performing a test on the sample collected with the diagnostic consumable.

18. The method of claim 17, further comprising:
if the diagnostic consumable is linked with patient ID information, transmitting instructions to the diagnostic engine to perform a test on the sample collected with the diagnostic consumable.

19. The method of claim 17, wherein at least one of the receiving ID information of a patient and the receiving ID information of a diagnostic consumable includes scanning a barcode.

20. An instrument data manager (IDM) configured to control operation of a plurality of diagnostic engines comprising:
a display;
a processor coupled to the display; and
a memory coupled to the processor, the memory having stored therein a plurality of computer executable instructions that, when executed by the processor, cause the IDM to:
receive via a user interface identification (ID) information for patients and ID information for diagnostic consumables;
link via a data structure stored in the memory the diagnostic consumable ID information with the patient ID information;
receive diagnostic consumable ID information from the plurality of diagnostic engines; and
transmit instructions to prevent testing of samples collected with diagnostic consumables at one or more of the plurality of diagnostic engines if diagnostic consumable ID information received from the one or more of the plurality of diagnostic engines is not linked to patient ID information stored in the memory.

* * * * *